(12) United States Patent
Huang et al.

(10) Patent No.: US 10,639,372 B2
(45) Date of Patent: May 5, 2020

(54) NUCLEIC ACID, MEDICAL NANOPARTICLE, AND PHARMACEUTICAL COMPOSITION THEREOF

(71) Applicant: Chung Yuan Christian University, Taoyuan (TW)

(72) Inventors: Leaf Huang, Taoyuan (TW); Yih-Chih Hsu, Taoyuan (TW); Gang Zheng, Taoyuan (TW); Chia-Hsien Yeh, Taoyuan (TW)

(73) Assignee: CHUNG YUAN CHRISTIAN UNIVERSITY, Taoyuan (TW)

( * ) Notice: Subject to any disclaimer, the term of this patent is extended or adjusted under 35 U.S.C. 154(b) by 976 days.

(21) Appl. No.: 15/184,481

(22) Filed: Jun. 16, 2016

(65) Prior Publication Data

US 2017/0360933 A1 Dec. 21, 2017

(51) Int. Cl.
| | | |
|---|---|---|
| *A61K 41/00* | (2020.01) | |
| *A61K 9/127* | (2006.01) | |
| *C12N 15/113* | (2010.01) | |
| *A61K 31/7088* | (2006.01) | |
| *C12N 15/11* | (2006.01) | |
| *A61K 47/69* | (2017.01) | |

(52) U.S. Cl.
CPC ........ *A61K 41/0071* (2013.01); *A61K 9/1271* (2013.01); *A61K 31/7088* (2013.01); *A61K 47/6911* (2017.08); *C12N 15/111* (2013.01); *C12N 15/1138* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2005/0196343 A1* | 9/2005 | Reddy | A61K 31/7072 424/9.322 |
| 2015/0246137 A1* | 9/2015 | Guo | A61K 9/127 424/450 |

FOREIGN PATENT DOCUMENTS

WO WO-2014052634 A1 * 4/2014

* cited by examiner

*Primary Examiner* — Michael D Burkhart
(74) *Attorney, Agent, or Firm* — Muncy, Geissler, Olds & Lowe, P.C.

(57) ABSTRACT

A medical nanoparticle includes a core, an outer lipid layer, an inner lipid layer, a photosensitizer, and a nucleic acid. The core includes a bio-degradable ionic precipitate (BIP). The inner lipid layer is between the core and the outer lipid layer. The photosensitizer is between the inner lipid layer and the outer lipid layer, and the nucleic acid is at the surface of the core.

18 Claims, 11 Drawing Sheets
Specification includes a Sequence Listing.

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: EGFR siRNA

<400> SEQUENCE: 1
aagtgctgga tgatagacgc adtdt                    25

```
<210> SEQ ID NO 2
<211> LENGTH: 21
<212> TYPE: DNA
<213> ORGANISM: Artificial Sequence
<220> FEATURE:
<223> OTHER INFORMATION: EGFR siRNA

<400> SEQUENCE: 2
gaaggaaacu gaauucaaau u                                              21
```

NUCLEIC ACID, MEDICAL NANOPARTICLE, AND PHARMACEUTICAL COMPOSITION THEREOF

BACKGROUND

Technical Field

The instant disclosure relates to a novel nanoparticle, in particular, to a nucleic acid, a medical nanoparticle, and a pharmaceutical composition thereof.

Related Art

Cancer, also called malignant tumor, is a disease in which the cells of a creature are proliferating abnormally and the proliferating cells would further invade and attack other tissues or organs of the creature. By statistics, around 14.1 million people got cancer in 2012 on the earth, and nearly 8.2 million people died from cancer, which counts 14.6% of the total death number in the year. The common cancers for male are the lung cancer, the prostate cancer, the colorectal cancer, and the stomach cancer; the common cancers for female are the breast cancer, the colorectal cancer, the lung cancer, and the cervical cancer; while the common cancers for child are the acute lymphoblastic leukemia and the brain cancer. Reasons leading to the cancers are complex and diverse. For example, genetic factors, obesity, smoking, drinking, lacking exercise, infection, radiation, dietary habits, and chronic inflammation may possibly cause the cells to be cancerated. In 2015, the study of The Johns Hopkins University in the United States further reported cancer generation might be related to luck; that is, cancer is generated by random mutation during the cell division. Nevertheless, the exact reason for leading the cancers is still unclear, increasing the difficulty in cancer precaution and therapy.

Many studies showed that, as compared with normal cells, cancer cells have following characters: (a) high metabolism rate; (b) immortalization, the cancer cells can be divided into more cells continuously and do not die or get aging; (c) the genes of the cancer cells are extremely unstable, the cancer cells are prone to have mutation and prone to have drug resistances; (d) the cancer cells can produce a plenty of growth factors like vascular endothelial growth factor (VEGF), epidermal growth factor (EGF), fibroblast growth factor (FGF), hepatocyte growth factor (HGF), etc., so that the cancer cells can proliferate rapidly and induce the growth of vessels; and (e) high invading and transferring ability. Currently, cancer therapies are mainly based on surgery; i.e., cutting off the cancer cells. Besides surgery, health workers may optionally use chemical therapy, radiation therapy, immunotherapy, or monoclonal antibody therapy based on the features of the cancer, the needs of the patient, or the condition of the patient. However, because of the aforementioned characteristics of cancer, these therapies cannot provide expected performances, no matter from an individual use or a combinational use of the therapies. Moreover, most of the therapies lack the specificity for cancer cells. Therefore, after the therapies are applied to the patient, not only the cancer cells are killed, but also the surrounding normal cells. Hence, the patient would have unpreventable side effects and harms in his or her health. Furthermore, after the cancer is transferred, the growth of the cancer cells cannot be efficiently suppressed anymore, the tissues or organs of the patient would be attacked by the cancer cells, and eventually leading the death of the patient.

SUMMARY

Because cancer is still thought to be an untreatable disease currently, and all conventional therapies fail to perform a desired efficacy. Related personnel are devoted in developing a way for efficient cancer treatment to reduce the pain and the discomfort of the patient.

A medical nanoparticle comprises a core, an outer lipid layer, an inner lipid layer, and a photosensitizer. The core comprises a bio-degradable ion precipitate (BIP). The inner lipid layer is between the core and the outer lipid layer. The photosensitizer is between the inner lipid layer and the outer lipid layer. The photosensitizer is pyropheophorbide-phosphatidic acid (pyro-PA).

A medical nanoparticle comprises a core, an outer lipid layer, an inner lipid layer, and a nucleic acid. The core comprises a bio-degradable ion precipitate (BIP). The inner lipid layer is between the core and the outer lipid layer. The nucleic acid is at the surface of the core, and the nucleic acid comprises a nucleotide sequence having the sequence set forth in SEQ ID NO: 1.

A medical nanoparticle comprises a core, an outer lipid layer, an inner lipid layer, a photosensitizer, and a nucleic acid being capable of suppressing expressions and functions of an epidermal growth factor receptor. The core comprises a bio-degradable ion precipitate (BIP). The inner lipid layer is between the core and the outer lipid layer. The photosensitizer is between the inner lipid layer and the outer lipid layer. The nucleic acid is at the surface of the core.

A pharmaceutical composition comprises a pharmaceutically acceptable excipient and one of the aforementioned nanoparticles.

A nucleic acid comprises a nucleotide sequence having the sequence set forth in SEQ ID NO: 1.

A pharmaceutical composition comprises the aforementioned nucleic acid and a pharmaceutically acceptable excipient.

Based on the above, in some embodiments, the nucleic acids, the medical nanoparticles having the nucleic acid, and/or the pharmaceutical compositions thereof can be applied to suppress the expressions and the functions of the EGFR by the nucleic acid (for example, a small hairpin ribonucleic acid), so that the growth of the cancer cells can be suppressed and/or the death of the cancer cells can be promoted. In some embodiments, the photosensitizer in the medical nanoparticle will release free radicals after being illuminated or excited by a light having certain wavelengths and the free radicals will cause the oxidative damages of cell targets to achieve the therapeutic efficacy on tumors. In some embodiments, the photosensitizer in the medical nanoparticle is suitable for the cancer diagnosis. In addition, in some embodiments, because of the coexistence of the nucleic acid and the photosensitizer, the nucleic acid and the photosensitizer can be applied to cure the tumor by different suppressing paths to achieve a better therapeutic efficacy.

BRIEF DESCRIPTION OF THE DRAWINGS

The disclosure will become more fully understood from the detailed description given herein below for illustration only, and thus not limitative of the disclosure, wherein.

DETAILED DESCRIPTION

Figure 1A:
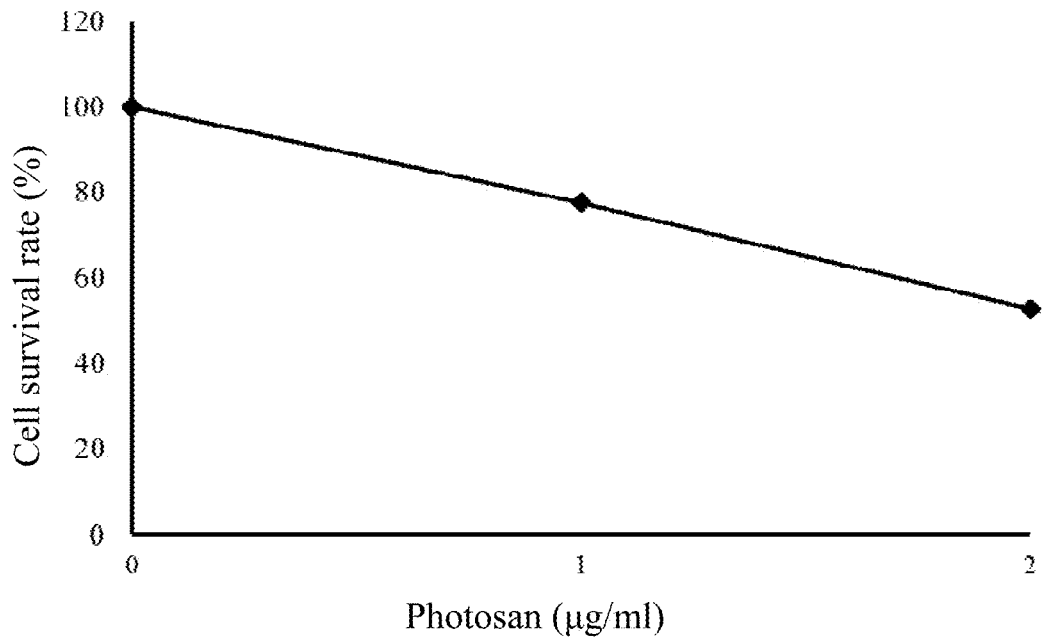
FIG. 1A illustrates a graph showing the MTT test result described in a first experimental example, wherein after the SCC4 cells are treated by the photosan molecule, the survival rate of the SCC4 cells are analyzed by the MTT test.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values, and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the instant disclosure and attaching claims are approximations that can vary as desired. At the very least, each numerical parameter should at least be construed in light of the number of reported significant digits and by applying ordinary rounding techniques.

Unless defined otherwise, all technical and scientific terms used herein have the same meaning as commonly understood by one of the ordinary skill in the art to which this invention belongs. The singular forms "a", "and", and "the" are used herein to include plural referents unless the context clearly dictates otherwise; conversely, terms with the plural forms used herein include singular referents.

As used herein, terms "Nucleotide sequence", "polynucleotide" or "nucleic acid" can be used interchangeably and are understood to mean, according to the present disclosure, either a double-stranded DNA, a single-stranded DNA or products of transcription of the said DNAs (e.g., RNA molecules). It should also be understood that the present disclosure does not relate to genomic polynucleotide sequences in their natural environment or natural state.

As used herein, the term "ribonucleic acid interference (RNAi)" indicates the RNA molecules for silencing or reducing the gene expression; RNAi includes small interference ribonucleic acids (siRNA), small hairpin ribonucleic acids (shRNA), and micro-ribonucleic acids (miRNA). In general, these RNA molecules and silent gene sequences are homogenous, so that these RNA molecules produce post-transcript silent gene having sequence specificity in an animal body or in a plant. These RNA molecules may be endogenous or exogenous, or may be integrated with the chromosome or may be expressed by the transfection vector out of the chromosome. Regarding the function, these RNA molecules may be applied to suppress the expressions of the target genes completely or partially; alternatively, these RNA molecules may be applied to suppress the functions of the target genes completely or partially to generate a silencing function.

As used herein, the term "therapy" means applying or treating a subject having cancer-related signs and/or cancer-related symptoms with the nucleic acids, the medical nanoparticles, and/or the pharmaceutical compositions thereof according any embodiment of the instant disclosure, so that the occurrences of the signs, the symptoms, the course of disease, the clinical markers, or the combination thereof of one or more cancers can be partially or completely suppressed, healed, postponed, inhibited, ceased, or reduced. Specifically, the cancer-related signs and symptoms may comprise, but not limited to, swelling, bleeding, pain, ulcer, lymph node enlargement, cough, hemoptysis, hepatomegaly, bone pain, bone fracture, body weight loss, loss of appetite, anemia, or the combination thereof. Herein, the term "therapy" may also mean applying a subject having early cancer-related signs or symptoms with the nucleic acids, the medical nanoparticles, and/or the pharmaceutical compositions thereof according any embodiment of the instant disclosure to reduce the risk of the signs or symptoms becoming cancers.

Specifically, the term "subject" means animals including human species that is treatable with the nucleic acids, the medical nanoparticles, and/or the pharmaceutical compositions thereof according any embodiment of the instant disclosure. Unless being specified, the term "subject" is intended to refer to both the male and female gender; the subject may be of different ages, for example, the subject may be a child or an adult.

The term "effective amount" as referred to herein designates the quantity of a component which is sufficient to yield a desired response. The specific effective or sufficient amount will vary with such factors as the particular condition being treated, the physical condition of the patient (e.g., the patient's body mass, age, or gender), the type of mammal or animal being treated (for example, the subject may be a rabbit, a mouse, an ape, a monkey, a human, and so forth), the duration of the treatment, the nature of concurrent therapy (if any), and the specific formulations employed and the structure of the compounds or its derivatives. For therapeutic purposes, the effective amount is also one in which any toxic or detrimental effects of the compound or composition are outweighed by the therapeutically beneficial effects. Effective amount may be expressed, for example, in grams, milligrams or micrograms or as milligrams per kilogram of body weight (mg/kg). Alternatively, the effective amount may be denoted by the concentration of the active ingredient of the pharmaceutical composition; the concentration may be, for example, a molar concentration, a mass concentration, a volume concentration, a molality, a mole fraction, a mass fraction, or a mixing ratio. It is understood that the person who has ordinary skills in the art can calculate the human equivalent dose (HED) of the drug (e.g., the nucleic acids, the medical nanoparticles, and/or the pharmaceutical compositions thereof according any embodiment of the instant disclosure) based on the drug dosage applied to an animal subject. For example, the person who has ordinary skills in the art can calculate the maximum safe dose of the drug based on the "Estimating the Maximum Safe Starting Dose in Initial Clinical Trials for Therapeutics in Adult Healthy Volunteers" published by the US Food and Drug Administration (FDA).

As used herein, the term "photodynamic therapy" refers to using a visible light (commonly generated by a non-thermal laser) to excite a photosensitizer to treat the tumor.

As used herein, the term "photodynamic diagnosis" refers to using a visible light (commonly generated by a non-thermal laser) to excite a photosensitizer to diagnose the tumor. After a photosensitizer molecule absorbs the energy of a certain wavelength of a light and excited by the light from a ground state to an excited state, if the photosensitizer molecule release the energy directly at its excited singlet state, the photosensitize molecule will emit a detectable fluorescence and go back to its ground state. Accordingly, the location of the tumor or the cancer can be diagnosed by the fluorescence of the photosensitizer.

As used herein, the term "pharmaceutical composition" includes a composition having one or more active ingredients (e.g., the nucleic acids, the medical nanoparticles, and/or the pharmaceutical compositions thereof according any embodiment of the instant disclosure) suitable for the therapeutic applications.

As used herein, a "pharmaceutically acceptable excipient" is one that is suitable for use with the subjects without undue adverse side effects (such as toxicity, irritation, and allergic response) commensurate with a reasonable benefit/risk ratio. Also, each excipient must be "acceptable" in the sense of being compatible with the other ingredients of the pharmaceutical composition. The excipient can be in the form of solid, semi-solid, or liquid diluent, cream, or a capsule.

Figure 3A:
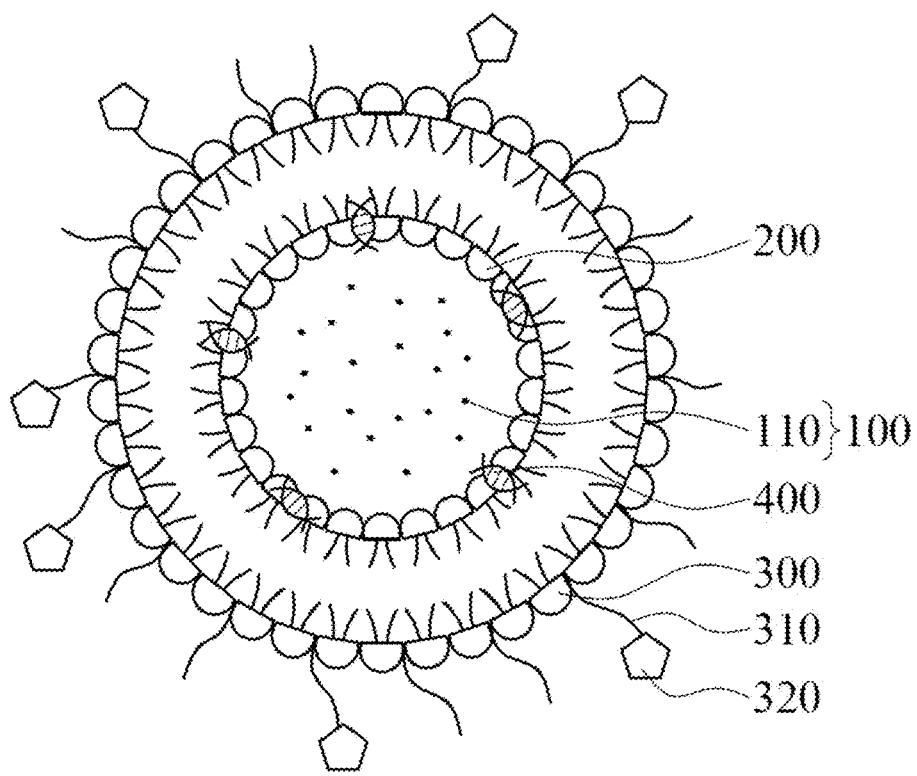
FIG. 3A illustrates a schematic view of a medical nanoparticle according to one embodiment of the instant disclosure.

In one embodiment, as shown in FIG. 3A, a medical nanoparticle comprises a nanoparticle (hereinafter called first nanoparticle). The first nanoparticle comprises a core, an outer lipid layer, an inner lipid layer, and a nucleic acid. The core comprises a bio-degradable ionic precipitate (BIP). The inner lipid layer is between the core and the outer lipid layer, and the nucleic acid is at the surface of the core. In some embodiments, the inner lipid layer may be the surface of the core, and the nucleic acid is embedded in the inner lipid layer. In other words, one of two ends of the nucleic acid is in the core, and the other end of the nucleic acid is out of the core.

Figure 3B:
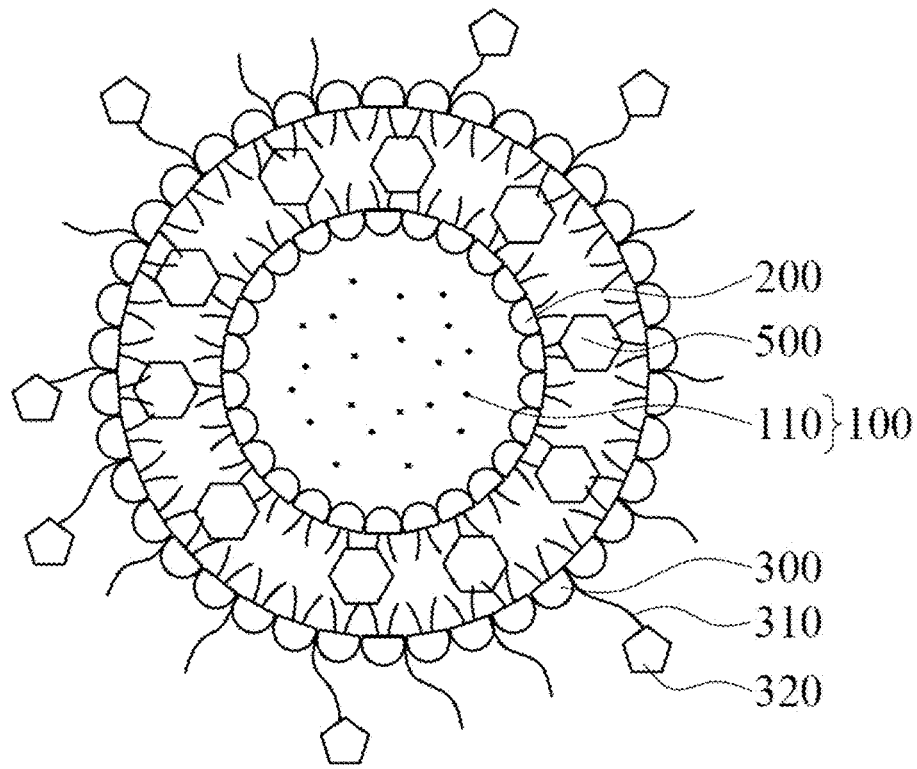
FIG. 3B illustrates a schematic view of a medical nanoparticle according to another embodiment of the instant disclosure.

In another embodiment, as shown in FIG. 3B, a medical nanoparticle comprises a nanoparticle (hereinafter called second nanoparticle). The second nanoparticle comprises a core, an outer lipid layer, an inner lipid layer, and a photosensitizer. The core comprises a bio-degradable ionic precipitate (BIP). The inner lipid layer is between the core and the outer lipid layer, and the photosensitizer is at the surface of the inner lipid layer and between the outer lipid layer and the inner lipid layer. In some embodiments, the photosensitizer is linked to the inner lipid layer.

In yet another embodiment, a medical nanoparticle comprises the foregoing first nanoparticle and the foregoing second nanoparticle.

Figure 3C:
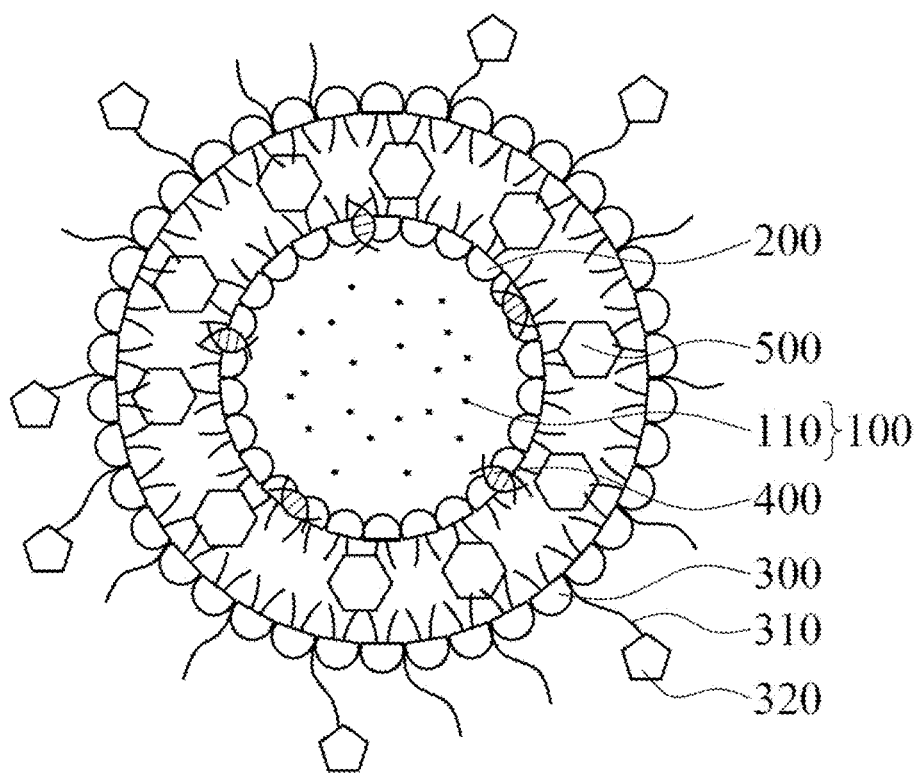
FIG. 3C illustrates a schematic view of a medical nanoparticle according yet another embodiment of the instant disclosure.

In further another embodiment, as shown in FIG. 3C, a medical nanoparticle comprises a core, an outer lipid layer, an inner lipid layer, a photosensitizer, and a nucleic acid. The core comprises a bio-degradable ionic precipitate (BIP). The inner lipid layer is between the core and the outer lipid layer, and the photosensitizer is at the surface of the inner lipid layer and between the outer lipid layer and the inner lipid layer. The nucleic acid is at the surface of the core. In some embodiments, the inner lipid layer may be the surface of the core, and the nucleic acid is embedded in the inner lipid layer. In other words, one of two ends of the nucleic acid is in the core, and the other end of the nucleic acid is out of the core. In some embodiments, the photosensitizer is linked to the inner lipid layer.

Wherein, the nucleic acid according to any of the foregoing embodiments has the ability to suppress expressions and functions of an epidermal growth factor receptor (EGFR). The EGFR is a cell surface receptor. After the EGFR combines with an epidermal growth factor (EGF), downstream enzymes (e.g., protein kinase C (PKC), extracellular signal-regulated kinase (ERK), protein kinase B (AKT), and Janus kinase (JAK)) will be activated to facilitate the cell growth and suppress the cell death. In addition, it is realized that the EGFR is overexpressed on many kinds of cancer cells and participating the cancerate reaction of the cancer cells. Accordingly, the nucleic acids, the medical nanoparticles having the nucleic acid, and/or the pharmaceutical compositions thereof according any embodiment of the instant disclosure can be applied to suppress the expressions and the functions of the EGFR by the nucleic acid (for example, a small hairpin ribonucleic acid), so that the growth of the cancer cells can be suppressed and/or the death of the cancer cells can be promoted.

Wherein, the photosensitizer according to any of the foregoing embodiments will release free radicals after being illuminated or excited by a light having certain wavelengths, and the free radicals will cause the oxidative damages of cell targets (e.g., cell membranes, organelles, enzymes, or DNAs) to achieve the therapeutic efficacy on tumors. In addition, after the photosensitizer is illuminated or excited by a light having certain wavelengths, the excited photosensitizer will emit fluorescence, so that the cancer diagnosis may be approached by the detection of the fluorescence. In addition, when a dye is illuminated or excited by a light having certain wavelengths, the dye will emit visible or invisible light, and the cancer diagnosis may be approached by the detection of the visible or invisible light. For example, the light emitted by the dye may be fluorescence, luminescence, ultraviolet ray, visible ray, or infrared ray; as long as the light emitted by the dye can be detected by a photodetector, the dye is suitable for the cancer diagnosis.

Furthermore, the medical nanoparticle according to any of the foregoing embodiments can enter into and stay in the cancer cells to kill or suppress the cancer cells by the enhanced permeability and retention effect (EPR effect). In general, as compared with a normal tissue or a normal organ, most solid tumors have: (a) higher vessel densities; (b) structure deficient vessels (for example, the solid tumor may have a huge gap between the endothelial cells thereof or the solid tumor may be lack of the smooth muscle layer); and (c) incomplete development of the lymph system. On one hand, these characters allow certain substances entering into and accumulating in the solid tumor; on the other hand, these characters allow the aforementioned substances not being eliminated by the immune cells easily, namely, the EPR effect. Therefore, the medical nanoparticles can be specifically targeted to certain cancer cells via the EPR effect. Wherein, the cancer cells may be cancer cells oriented from the prostate cancer, the lung cancer, the breast cancer, the melanotic cancer, the blood cancer, the pancreas cancer, the ovarian cancer, the liver cancer, the colorectal cancer, the neuroblastoma, the glioblastoma, the head and neck cancer, or the oral cancer.

In addition, in some embodiments, because of the coexistence of the nucleic acid and the photosensitizer, the nucleic acid and the photosensitizer can be applied to cure the tumor by different suppressing paths to achieve a better therapeutic efficacy.

In some embodiments, the nucleic acid according to any of the foregoing embodiment may comprise a nucleotide sequence having the sequence set forth in SEQ ID NO: 1. In other some embodiments, the nucleic acid may comprise a nucleotide sequence having the sequence set forth in SEQ ID NO: 2.

In some embodiments, the nucleic acid according to any of the foregoing embodiment may be ribonucleic acid interference (RNAi).

In some embodiments, the RNAi molecule may be a small interference ribonucleic acid (siRNA). Specifically, the siRNA molecule may be double stained and have a blunt, a 3'-overhang, or a 5'-overhang. In some embodiments, the siRNA molecule may have a blunt, and the positive strand of the siRNA molecule comprises a nucleotide sequence having the sequence set forth in SEQ ID NO: 1 or SEQ ID NO: 2.

In some embodiments, the RNAi molecule may be a small hairpin ribonucleic acid (shRNA). Specifically, the shRNA molecule has a spacer formed by a small bit of nucleic acids to connect its positive strain with its negative strain, so that the shRNA molecule is formed as a loop structure. In some embodiments, the positive strand of the shRNA molecule comprises a nucleotide sequence having the sequence set forth in SEQ ID NO: 1 or SEQ ID NO: 2.

In further some embodiments, the RNAi molecule may be a micro-ribonucleic acid (miRNA) or a primer of the micro-ribonucleic acid (pri-miRNA)/a precursor of the micro-ribonucleic acid (pre-miRNA). In some embodiments, the miRNA molecule or its primer/precursor comprises a nucleotide sequence having the sequence set forth in SEQ ID NO: 1 or SEQ ID NO: 2.

In some embodiments, the photosensitizer according to any of the foregoing embodiments is selected from a group consisting of pyropheophorbide-phosphatidic acid (pyro-PA), photosan, photofrin (PH), tin etiopurpurin (SnET2), benzoporphyrin derivative (BPD), and 5-aminolaevulinic acid (ALA).

Wherein, pyropheophorbide is a chlorophyll derivative, and the pyro-PA molecule is a lipid derivative from the reaction of the pyropheophorbide and 1-palmitoyl-2-hydroxy-sn-glycero-3-phosphocholine. As compared to stand-alone pyro-PA molecule, the pyro-PA molecule enclosed in the medical nanoparticle has more apparent bioactivity. The light sources suitable for exciting the medical nanoparticle comprising the pyro-PA molecule are lights with wavelengths between 400 to 1000 nm. Lights with different wavelengths may be applied to excite the pyro-PA molecule according to different needs. For example, to cure a superficial cancer, blue, green, or yellow lights with wavelengths between 400 to 600 nm can be provided as the excitation source; while to cure a deep cancer, red or near infrared lights with wavelengths between 600 to 1000 nm can be provided as the excitation source. In one embodiment, the medical nanoparticle comprising the pyro-PA molecule may be excited by a light with a wavelength of 410 nm, so that free radicals are generated to kill the cancer cells.

In some embodiments, the BIP is selected from a group consisting of calcium phosphate (CaP), calcium citrate, calcium carbonate, magnesium carbonate, magnesium phosphate, and manganese phosphate. For example, if the BIP is the CaP molecule, in preparation, calcium chloride ($CaCl_2$), sodium hydrogen phosphate ($Na_2HPO_4$), and the nucleic acid (if ever have) are mixed with each other uniformly, and then a core comprising the CaP molecule and the nucleic acid is formed by the attraction between positive and negative charges of the molecules.

In some embodiments, the inner lipid layer and the outer lipid layer form a double lipid layer structure for improving the stability of the medical nanoparticle in solution and for improving the absorption of the medical nanoparticle to cells of the subject.

In some embodiments, the inner lipid layer may encloses the core and combines with the core by the feature of the attraction between cations and anions.

In some embodiments, the inner lipid layer may be an anion lipid layer, and the outer lipid layer is a cation lipid layer. Wherein, the cation lipid layer encloses the anion lipid layer by the feature of the attraction between cations and anions.

In some embodiments, the inner lipid layer may be an anion lipid layer, and the outer lipid layer is a neutral lipid layer. Wherein, the neutral lipid layer encloses the anion lipid layer by the feature of the gathering of hydrophobic ends of lipids.

In some embodiments, the anion lipid layer may comprise, but not limited to, dioleoyl phosphatidic acid (DOPA), 2,3-dimercapto-1-propanesulfonic acid (DMPS), 1,2-dipalmitoyl-sn-glycero-3-phosphoserine (DPPS), dioleoyl phosphatidylserine (DOPS), palmitoyl oleoyl phosphatidylserine (POPS), 1,2-dimyristoyl-sn-glycero-3-phosphoglycerol (DMPG), 1,2-dipalmitoyl-sn-glycero-3-phosphoglycerol (DPPG), 1,2-dioleoyl glycero-3-phospho-1-glycerol (DOPG), palmitoyl oleoyl phosphatidylglycerol (POPG), dimyristoyl phosphatidic acid (DMPA), dipalmitoyl phosphatidic acid (DPPA), dioleoyl phosphatidic acid (DOPA), palmitoyl oleoyl phosphatidic acid (POPA), cholesteryl hemisuccinate (CHEMS), or derivatives thereof.

In some embodiments, the cation lipid layer may comprise, but not limited to, 1,2-dioleoyl-3-trimethylammonium-propane chloride salt (DOTAP), dimyristoyl trimethylammonium propane (DMTAP), 1,2-dipalmitoyl-3-trimethylammonium propane (DPTAP), deacylated phosphatidylinositol manno-oligosaccharides (dPIMs), 1,2-dioleoyl oxypropyl-3-dimethyl hydroxyethyl ammonium bromide (DORIE), dimethyl dioctadecylammonium bromide (DAAB), 1,2-dioleoyl-3-dimethylammonium propane (DODAP), 1,2-dioleoyl-sn-glycero-3-ethyl phosphocholine (DOEPC), or derivatives thereof.

In some embodiments, the neutral lipid layer may comprise, but not limited to, dioleoyl phosphatidylcholine (DOPC), 1-palmitoyl-2-oleoyl-sn-glycero-3-phosphocholine (POPC), 1,2-dioleoyl-sn-glycero-3-phosphoethanolamine (DOPE), or derivatives thereof.

Therefore, according to the aforementioned embodiment in which the CaP molecules are taken as the BIP, if the anion lipid layer is the DOPA molecules and the cation lipid layer is the DOTAP molecules, in preparation, the core comprising the CaP molecules and the nucleic acid (if ever have) is mixed with the DOPA molecules. The calcium ions of the core will react with the phosphate ions of the DOPA molecules, so that the DOPA molecules enclose the core and form the inner lipid layer. Next, the DOTAP molecules are added, and the DOTAP molecules enclose the inner lipid layer to form the outer lipid layer based on the feature of the attraction between cations and anions.

In some embodiments, as shown in FIGS. 3A to 3C, the medical nanoparticle further comprise a lipid-polyethylene glycol (PEG) conjugate, and the lipid-PEG conjugate is linked to the outer lipid layer.

The lipid-PEG conjugate comprises a lipid and the PEG polymer. Wherein, the lipid is for connecting the PEG polymer with the outer lipid layer. The PEG polymer is a polymer for increasing the circulation lifetime of liposome, and the PEG polymer is commonly used in connecting a certain molecule (e.g., an antibody, a drug, a protein peptide, or a ligand) to the surface of the liposome. In addition, the PEG polymer has a high degree of freedom because it is a polymer having a certain length, so that the medical nanoparticles can be efficiently shielded by the PEG polymer and prevented from being attacked by macrophages or leukocytes. For the preparation of a medical nanoparticle having the conjugates, firstly, the PEG polymer is binding to the lipid followed by the addition of the certain molecule, so that the lipid-PEG-certain molecule conjugate is formed. Next, in the preparation of the outer lipid layer, the conjugate is added and mixed with the outer lipid layer. Hence, the hydrophobic ends of the lipid of the conjugate are gathered with the hydrophobic ends of the outer lipid layer, so that the conjugate can be stably engaged into the outer lipid layer.

In some embodiments, the certain molecule may be a target agent for improving the specificity toward the cancer cells. In some embodiments, the target agent may be α-Enolase. In some embodiments, the target agent may be a benzamide derivative. In some embodiments, as shown in FIGS. 3A to 3C, the target agent is anisamide (AA). For example, in the preparation of the outer lipid layer, the DOTAP molecules are mixed with the lipid-PEG-AA conjugates, so that the AA molecules can be linked to the surface of the medical nanoparticle.

Because the AA molecule can be combined with a sigma receptor, and sigma receptor is a molecule overexpressed on the surface of cancer cells, the AA molecule can be provided as the target for targeting cancer cells. Accordingly, when the AA molecule is linked to the surface of a medical nanoparticle according any embodiment of the instant disclosure, the specificity and the therapeutic efficacy of the medical nanoparticle toward cancer cells can be improved. In addition, since the AA molecule can be targeted to the sigma receptor of the surface of the cancer cell, the medical nanoparticle having the AA molecule on the surface thereof can be specifically targeted to the cancer cells without killing or damaging the surrounding normal cells, so that the therapeutic efficacy can be improved.

Wherein, the lipid suitable for linking the PEG polymer may be, but not limited to, 1,2-dimyristoyl-sn-glycero-3-phosphoethanolamine (DMPE), 1,2-distearoyl-sn-glycero-3-phosphoethanolamine (DSPE), 1,2-dilauroyl-sn-glycero-3-phosphoethanolamine (DLPE), cholesterol, or oleic acid.

In some embodiments, the outer lipid layer may further comprise cholesterol. The cholesterol molecule is one of the essential elements for forming the cell membrane and the liposome. The cholesterol molecule has the ability to adjust the membrane mobility and the cholesterol molecule is called the buffering agent of the mobility of liposome. When the cholesterol molecule is added to the reaction, the stability of the liposome (i.e., the double lipid layer) can be improved. Therefore, in this embodiment, the DOTAP molecules, the lipid-PEG-AA conjugates, and the cholesterol molecules are mixed and expressed on the surface of the outer lipid layer of the medical nanoparticle.

In some embodiments, the medical nanoparticle has contents in certain amounts (i.e., the medical nanoparticle has the nucleic acid and the photosensitizer in certain amounts), so that the charges can be balanced to allow the stable formation of the medical nanoparticle. Specifically, if allowable, the medical nanoparticle comprises the nucleic acid and the photosensitizer having certain ratio or concentration for providing a better the therapeutic efficacy. In some embodiments, the weight ratio (μg/μg) between the nucleic acid and the photosensitizer of the medical nanoparticle is about 1:1 to 1:32; wherein, the concentration of the nucleic acid may be 1 to 10 milligrams per milliliter, while the concentration of the photosensitizer may be 10 to 50 milligrams per milliliter. In one embodiment, the weight ratio between the nucleic acid and the photosensitizer of the medical nanoparticle is about 1:16; wherein, the concentration of the nucleic acid may be 2 milligrams per milliliter, while the concentration of the photosensitizer may be 32 milligrams per milliliter.

In some embodiments, the core of the medical nanoparticle comprising the nucleic acid and the photosensitizer (including the inner lipid layer) has an average diameter of about 5 to 50 nm. For example, the diameter of the core may be, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm. In some embodiments, the average diameter of the core is about 5 to 30 nm. In some embodiments, the average diameter of the core is about 6 to 20 nm.

In some embodiments, the medical nanoparticle comprising the core enclosed by the double lipid layer has an average diameter of about 12 to 50 nm. That is, the diameter of the medical nanoparticle may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm. In some embodiments, the average diameter of the medical nanoparticle is about 15 to 20 nm. In some embodiments, the average diameter of the medical nanoparticle is about 20 nm.

In some embodiments, the medical nanoparticle comprising the core enclosed by the double lipid layer has a surface potential of 10 to 70 millivolt (mV). That is, the surface potential of the medical nanoparticle may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mV. In some embodiments, the surface potential of the medical nanoparticle may be 20 to 60 mV.

Furthermore, the nucleic acids or the medical nanoparticles according to any of the foregoing embodiments can be applied to produce a pharmaceutical composition. In other words, the pharmaceutical composition comprises the nucleic acids or the medical nanoparticles according to any of the foregoing embodiments.

Herein, the pharmaceutical composition is prepared in accordance with acceptable, established pharmaceutical procedures. The choice of a pharmaceutically acceptable excipient to be used in conjunction with the nucleic acid and the medical nanoparticle is basically determined by the desired product form of the pharmaceutical composition. Wherein, the excipient may be diluents, excipients, disintegrants, granulation binders, lubricants, fillers, sweetening or flavoring agents, coloring matter or dyes, emulsifiers, suspending agents, fatty acids, oils, dispersing agents, surfactants, bioavailability enhancers, or combination thereof.

In some embodiments, the pharmaceutical composition may be administered by any suitable route, for example, by oral, parenteral (such as intramuscular, intravenous, subcutaneous, or intraperitoneal injection), topical, or transmucosal administration.

For oral administration, the nucleic acids or the medical nanoparticles according to any of the foregoing embodiments may be formulated into tablets containing various excipients such as microcrystalline cellulose, sodium citrate, calcium carbonate, dicalcium phosphate, and glycine; along with various disintegrants such as starch, aiginic acid and certain silicates; together with granulation binders like polyvinyl pyrrolidone, sucrose, gelatin, and acacia. Additionally, lubricating agents such as magnesium stearate, sodium lauryl sulfate and talc may be added.

Solid composition may also be employed as fillers in gelatin capsules; preferred materials in this connection also include lactose or milk sugar as well as high molecular weight polyethylene glycols.

When aqueous suspensions and/or elixirs are desired for oral administration, the nucleic acids or the medical nanoparticles may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the nucleic acids or the medical nanoparticles may be formulated into liquid pharmaceutical compositions, which are sterile solutions, or suspensions that can be administered by, for example, intravenous, intramuscular, subcutaneous, or intraperitoneal injection. Suitable diluents or solvents for manufacturing sterile injectable solution or suspension include, but are not limited to, 1,3-butanedioi, mannitol, water, Ringer's solution, and isotonic sodium chloride solution. Fatty acids, such as oleic acid and its glyceride derivatives are also useful for preparing injectables, as are natural pharmaceutically acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For topical administration, the nucleic acids or the medical nanoparticles may be formulated into a variety of dosage forms for topical application. A wide variety of pharmaceutically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol, and gel-producing substances.

For transmucosal administration, the nucleic acids or the medical nanoparticles may also be formulated in a variety of dosage forms for mucosal application, such as buccal and/or sublingual drag dosage units for drag delivery through oral mucosal membranes. A wide variety of bio-degradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinyl pyrrolidone; dextran; guar gum; pectins; starches; and cellulosic polymers.

Depending on practical needs, the pharmaceutical composition may be in the form of solid, semi-solid, liquid, cream, capsule, spray, or patch. Accordingly, the pharmaceutical composition may be administered by any suitable route, for example, by oral, parenteral (such as intramuscular, intravenous, subcutaneous, or intraperitoneal injection), topical, or transmucosal administration, so that an optimal therapeutic efficacy can be provided toward different clinical conditions.

After the pharmaceutical composition is administrated to the subject, the pharmaceutical composition can be directed to the tumor by systemic circulation, and targeted to the cancer cells and/or cancerous tissues by the EPR effect of the medical nanoparticle and the AA molecule (or other target agents). Next, the medical nanoparticle can be fused with the cell membranes and can be absorbed by the cancer cells/tissues. Once the medical nanoparticle enters into the cell/tissue, the medical nanoparticle releases the EGFR siRNA to stop the expression of the epidermal growth factor, and further inhibit the growth and/or the cancer cells or facilitate the death of the cancer cells. In addition, if a proper illumination is provided to the medical nanoparticle, the pyro-PA molecule in the medical nanoparticle would be activated to generate free radicals to cause oxidative damages to the cancer cell/tissue.

As mentioned above, the pyro-PA molecule in the medical nanoparticle can be activated by a light source having wavelengths between 400 to 1000 nm. It is understood that, different wavelengths represent different excitation energies and may be adapted to cancers with different kinds, different positions, different characters, or different sizes. In one embodiment, the pyro-PA molecule in the medical nanoparticle may be activated by a light source having a wavelength of 410 nm.

The following Examples are provided to elucidate certain aspects of the instant disclosure and to aid those of skilled in the art in practicing this invention. These Examples are in no way to be considered to limit the scope of the invention in any manner. Without further elaboration, it is believed that one skilled in the art can, based on the description herein, utilize the instant disclosure to its fullest extent. All publications cited herein are hereby incorporated by reference in their entirety.

Cultivation of Oral Cancer Cells

The human oral cancer cells used in the Examples SCC4 and SAS are cultivated in a Dulbecco's Modified Eagle's medium (DMEM) cell culture having 10% fetal bovine serum (FBS). The cells are cultivated in an environment having 5% carbon dioxide in 37 degree Celsius. When enough cells are cultivated, the subsequent analysis and tests are performed.

Preparing Nanoparticle Enclosing EGFR siRNA

The siRNA is enclosed by lipid calcium phosphate (LCP). The CaP core of the nanoparticle is formed by the microemulsion reaction, followed by enclosing the CaP core with the DOTAP molecules and the PEG polymers. Because the AA molecules can be efficiently absorbed by the sigma receptor on the cancer cell membrane, the PEG polymers may be modified by the AA molecules for targeting to the cancer cells. The preparation is described as following. Firstly, the $CaCl_2$ molecules and the $Na_2HPO_4$ molecules are added to an oil phase (cyclohexane/lgepal CO-520) followed by adding the DOPA molecules and the EGFR siRNAs for forming the Cap as the core. Next, for filtering impurities, absolute ethanol is added into the mixture followed by centrifuging 10 minutes with 12500 rpm. Then, chloroform is added into the mixture followed by centrifuging with 10000 rpm. The supernatant is the LCP cores. Then, the DOTAP molecules, the cholesterol molecules, the DSPE-PEG conjugates, and the AA molecules (optionally) are added into the LCP core followed by nitrogen purging and vacuum pumping. By doing these steps, nanoparticle enclosing EGFR siRNA can be obtained.

Preparing Nanoparticle Enclosing Pyropheophorbide

The pyropheophorbide molecule is bound by a phosphatidic acid to form the pyro-PA molecule, so that the pyro-PA molecule can be embedded into the fluid mosaic phospholipid at the inner layer of the LCP because the pyro-PA molecule has both the hydrophilic and the hydrophobic features. Because the pyropheophorbide molecule is a photosensitizer and will have photochemical reaction with lights having certain wavelengths, the whole preparation should be away from light. The preparation of the nanoparticle enclosing Pyropheophorbide is described as following. Firstly, the $CaCl_2$ molecules and the $Na_2HPO_4$ molecules are added to an oil phase (cyclohexane/lgepal CO-520) followed by adding the DOPA molecules and the pyro-PA molecules for forming the Cap as the core. Next, for filtering impurities, absolute ethanol is added into the mixture followed by centrifuging 10 minutes with 12500 rpm. Then, chloroform is added into the mixture followed by centrifuging with 10000 rpm. The supernatant is the LCP cores. Then, the DOTAP molecules, the cholesterol molecules, the DSPE-PEG conjugates, and the AA molecules (optionally) are added into the LCP core followed by nitrogen purging and vacuum pumping. By doing these steps, nanoparticle enclosing Pyropheophorbide can be obtained.

Cytotoxicity Test (MTT Test)

The MTT reagent (namely, 3-(4,5-dimethylthiazol)-2,5-diphenyltetrazoliumbromide) is a yellow dye. After the MTT reagents are reacted with succinatedehydrogenase-ubiquinone (SDH) in the mitochondrion and cytochrome C, water insoluble blue-purple crystals are formed. After the crystals are dissolved in DMSO solution, the cell survival condition may be determined by the absorbance of the solution at 570 nm, so that the survival ratio of the cells can be calculated.

DMEM cell culture without serum are provided for preparing MTT solution having a concentration of 5 milligrams per milliliter. And then, a filter membrane having a pore diameter of 0.22 micrometers is provided for the filtration of solution, and the filtered solution is provided for applying in the subsequent cell tests.

The SCC4 or SAS cells are planted in a 48-well plate (each having $1 \times 10^4$ cells). These cells are then treated by the photosan molecules and the pyro-PA molecules for 48 hours. Next, 100 microliter saline solution is provided for washing the cells followed by the addition of 20 microliter MTT solution. After the cells are stayed in a cell cultivation box having 5% carbon dioxide at 37 degree Celsius for 4 hours, the MTT solution is removed and 300 microliter DMSO is added. Then, the cells are stayed away from light at room temperature for 30 minutes. Next, 200 microliter supernatant of the solution in each of the wells is taken to a 96-well plate. And then, the absorbance of the supernatant at 570 nm can be obtained by an enzyme-linked immunosorbent assay (ELISA) reader (model: VersaMax™ Microplate Reader, Molecular devices, Sunnyvale, USA).

Nanoparticle Analysis 1 microgram nanoparticle is dipped on a gold grid (Formvar carbon support film on specimen grid). After two days vacuum drying, the samples are provided for transmission electron microscope (model: HT7700, Hitachi, Japan) in Tsinghua University.

In Vivo Imaging System (IVIS) Analysis

In a first set of experiments of the IVIS analysis, cancer cell transfer can be observed. In the first set of experiments, genes in the firefly for luciferase coding are transplanted to the cancer cells. And then, cells having stable luciferase expression are selected by antibiotics. Next, these cells are injected to the right thighs of mices by subcutaneous injection. After the tumors grow to about 200 cubic millimeters, the mice are divided into groups (treated group and untreated group, depending on the experiments) for the therapy. Then, the in vivo imaging of the cancer cells can be obtained from the IVIS system (model: Lumina series III) and recorded.

In a second set of experiments, the transmission of the nanoparticles comprising photosensitizers in the mouse can be observed. In the second set of experiments, 200 microliter nanoparticles (comprising EGFR siRNA 2 milligrams per liter and photosensitizer 16 milligrams per liter) are injected into the mouse from the tail vein. And then, the mouse is placed away from light for 55 minutes. Before into the IVIS system, the mouse is anesthetize by gas anesthesia techniques. Then, the mouse is illuminated by a 660 nm light source in the IVIS for exciting the pyro-PA molecules in the nanoparticles. Next, the absorbances from 670 to 690 nm and from 710 to 730 nm are captured by photography.

Animal Test

The SCC4 cancer cells ($6\times10^5$) are planted to the subcutaneous tissue of mice (BALB/cAnN.Cg-foxn1nu/CrlNarl, 8 weeks). After the tumor grows to 200 cubic millimeters, nanoparticles (15 to 45 mM, 200 microliters) are injected into the mice from the tail veins. Then, the mice are placed away from light for 55 minutes followed by the illumination of a 410 nm light source for exciting the pyro-PA molecules in the nanoparticeles. And then, the absorbances from 670 to 690 nm and from 710 to 730 nm are measured.

At day 0, the SAS cancer cells ($6\times10^5$) are planted to the subcutaneous tissue of mice (BALB/cAnN.Cg-foxn1nu/Crl-Narl, 8 weeks). After the tumor grows to 200 cubic millimeters, nanoparticles (15 to 45 mM, 200 microliters) are injected into the mice from the tail veins by 3 dosages. Then, the mice are placed away from light for 55 minutes followed by the fixation of a mouse retainer, and a plant light (in the wavelength of visible lights) is provided for the therapy. The light energy is 100 joule per square centimeters. Next, the size of the tumor and the weight change of the mouse are measured daily.

First Experimental Example: Killing Performance for Different Photosensitizers

Figure 1B:
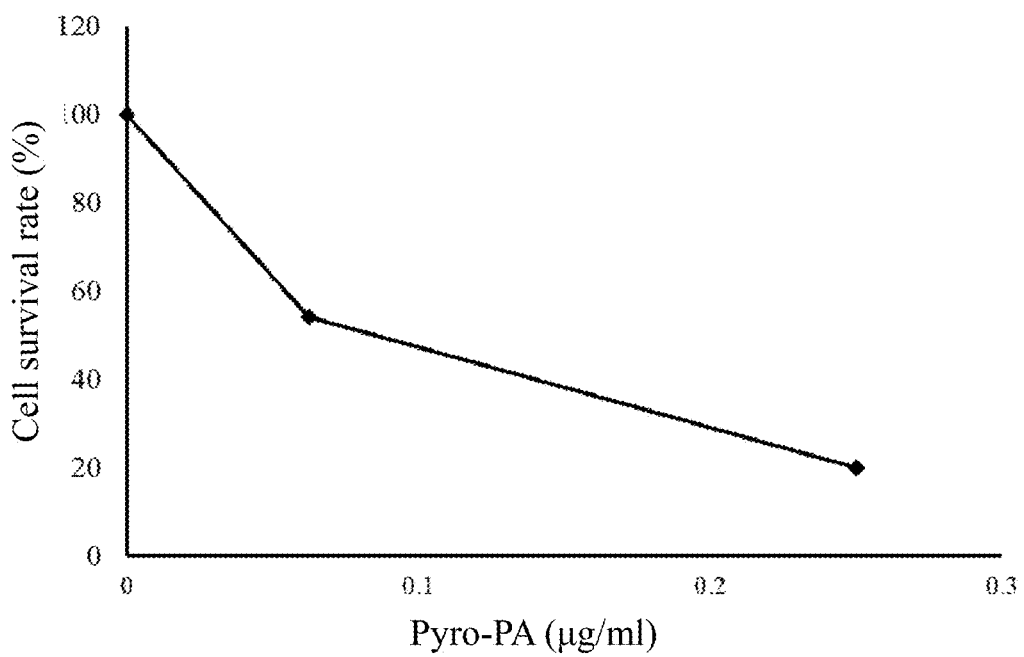
FIG. 1B illustrates a graph showing the MTT test result described in the first experimental example, wherein after the SCC4 cells are treated by pyropheophorbide-phosphatidic acid (pyro-PA), the survival rate of the SCC4 cells are analyzed by the MTT test.

FIGS. 1A and 1B respectively illustrate curves show the survival rates of the SCC4 cells treated by photosan molecules and pyro-PA molecules. From the equations of the curves, the concentration of 50% inhibition ($IC_{50}$) can be calculated. The result shows that, the $IC_{50}$ of photosan for SCC4 cells is 2.4 microgram per milliliter; conversely, the $IC_{50}$ of pyro-PA for SCC4 cells is 0.8 microgram per milliliter.

Figure 1C:
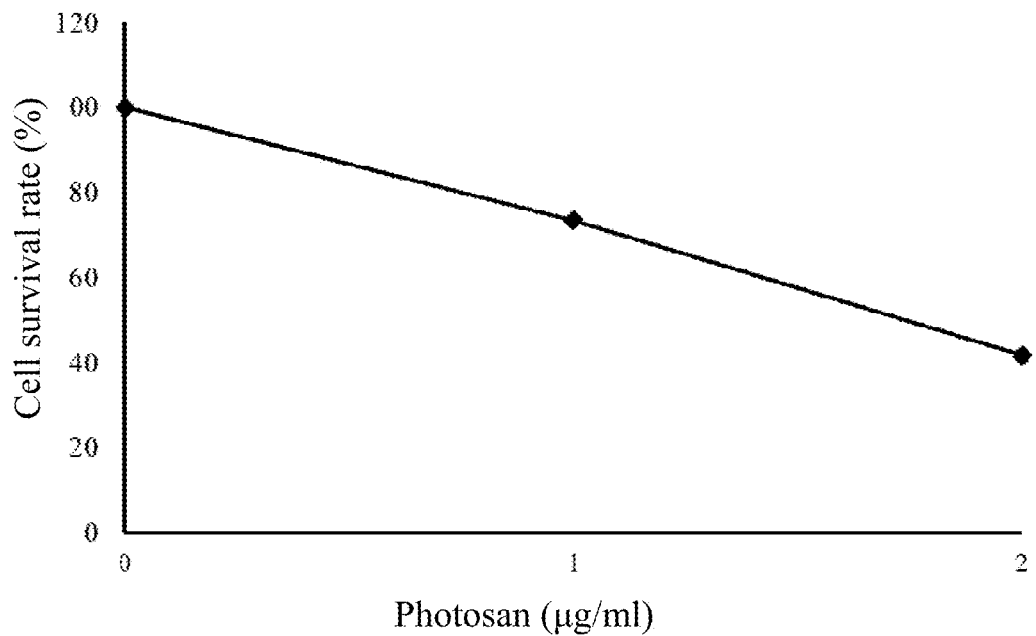
FIG. 1C illustrates a graph showing the MTT test result described in the first experimental example, wherein after the SAS cells are treated by the photosan molecule, the survival rate of the SAS cells are analyzed by the MTT test.
Figure 1D:
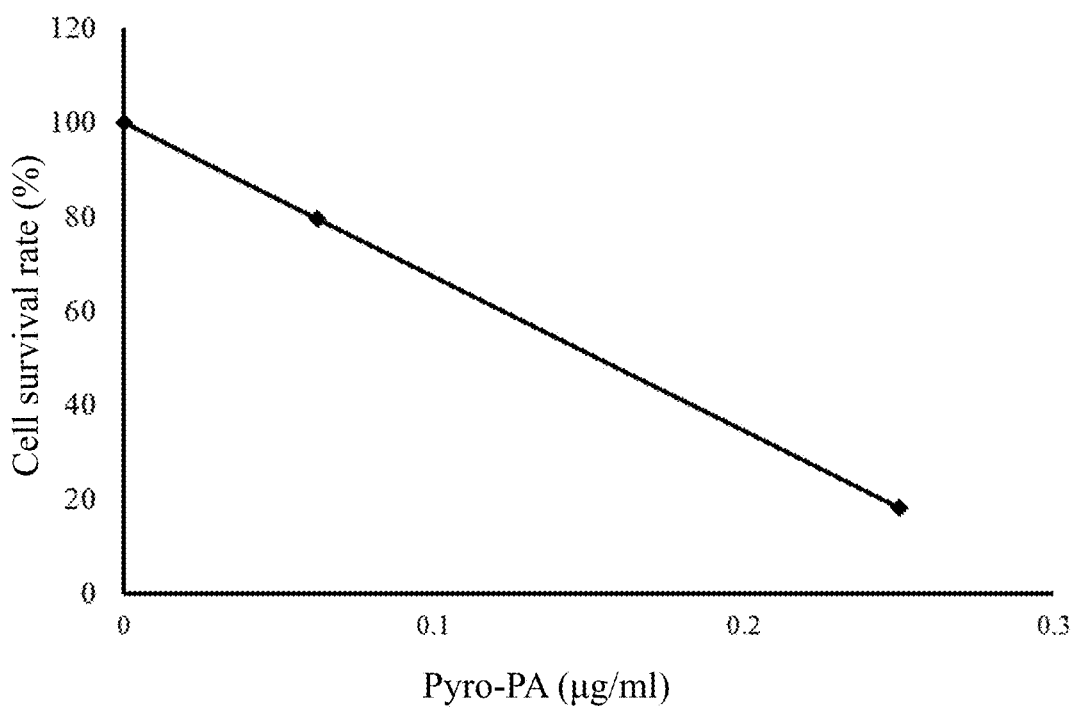
FIG. 1D illustrates a graph showing the MTT test result described in the first experimental example, wherein after the SAS cells are treated by the pyro-PA molecule, the survival rate of the SAS cells are analyzed by the MTT test.

Similarly, after the SAS cells are treated by the photosan molecules (as shown in FIG. 1C) and the pyro-PA molecules (as shown in FIG. 1D), the $IC_{50}$ of photosan for SAS cells is 1.75 microgram per milliliter, while the $IC_{50}$ of pyro-PA for SAS cells is 0.1 microgram per milliliter.

Figure 2A:
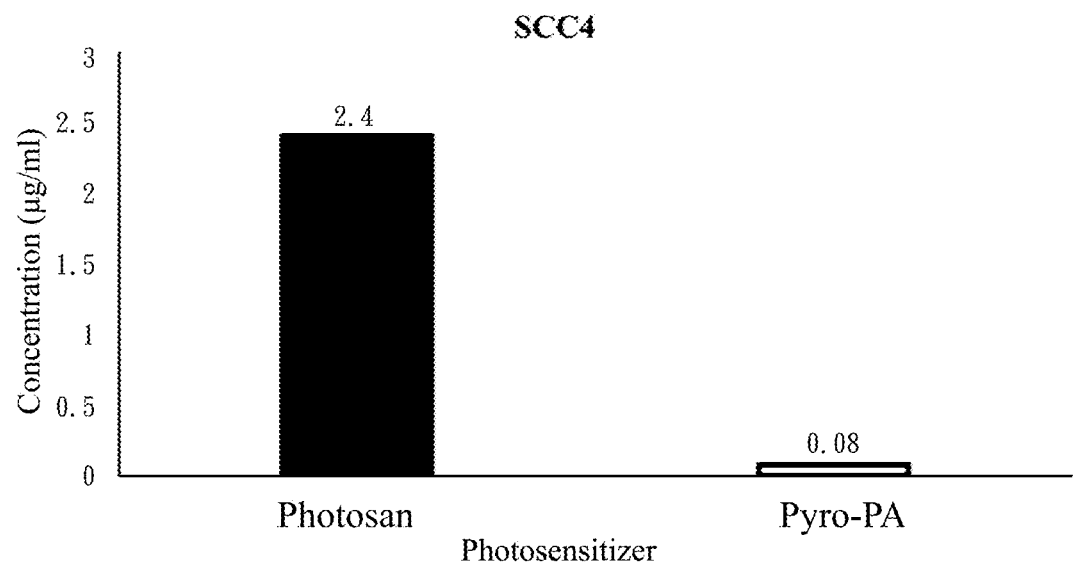
FIG. 2A illustrates a column graph of the first experimental example, wherein the SCC4 cells are respectively treated by the photosan molecule and the pyro-PA molecule, and then the MTT test is applied to analyze the survival rate of the SCC4 cells.
Figure 2B:
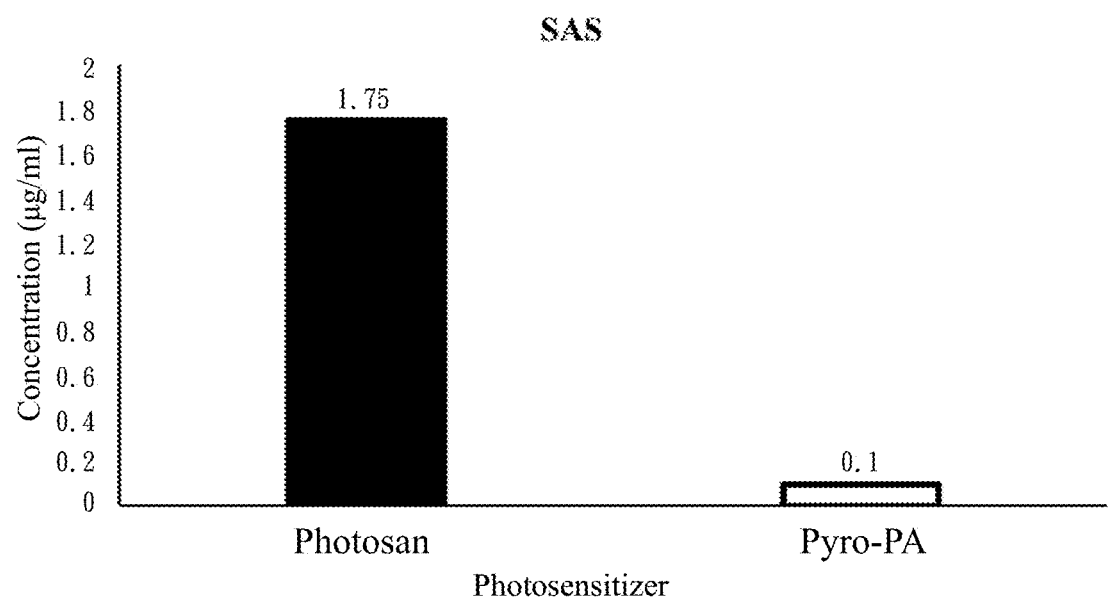
FIG. 2B illustrates a column graph of the first experimental example, wherein the SAS cells are respectively treated by the photosan molecule and the pyro-PA molecule, and then the MTT test is applied to analyze the survival rate of the SAS cells.

In FIGS. 2A and 2B, the results are further summarized for showing the difference of the killing performances between the two photosensitizers. From the figures, in SCC4 cells, the $IC_{50}$ of photosan for SCC4 cells is 2.4 microgram per milliliter, while the $IC_{50}$ of pyro-PA for SCC4 cells is 0.8 microgram per milliliter, 30 times smaller than the former; on the other hand, in SAS cells, the $IC_{50}$ of photosan for SAS cells is 1.75 microgram per milliliter, while the $IC_{50}$ of pyro-PA for SAS cells is 0.1 microgram per milliliter, 17.5 times smaller than the former.

Accordingly, the result shows that the pyro-PA molecules have a better suppression performance to cancer cells as compared to the photosan molecules. In the following experimental examples, the pyro-PA molecules are provided as the photosensitizer in the nanoparticles, and related analysis are performed.

Second Experimental Example: Optimum Capsulated Amount

After the pyro-PA molecules are confirmed as the photosensitizer in the nanoparticles, in the second experimental example, the optimum capsulated amounts of the EGFR siRNA and the pyro-PA molecule are analyzed.

Figure 4A:
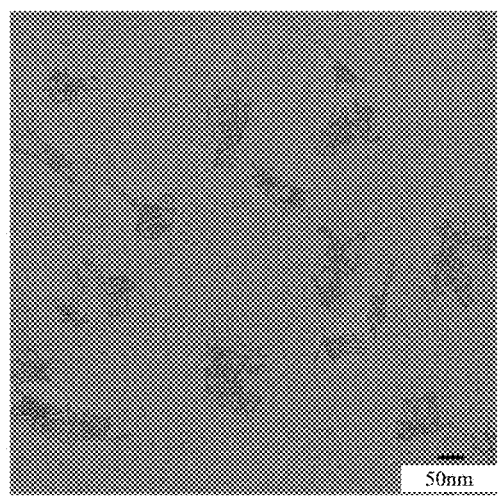
FIGS. 4A to 4C are electronic micrographs described in a second experimental example, wherein the nanoparticles have epidermal growth factor receptor small interference ribonucleic acids (EGFR siRNA) and the pyro-PA molecule with different concentrations, and the nanoparticles are further analyzed by the transmission electron microscopy.
Figure 4B:
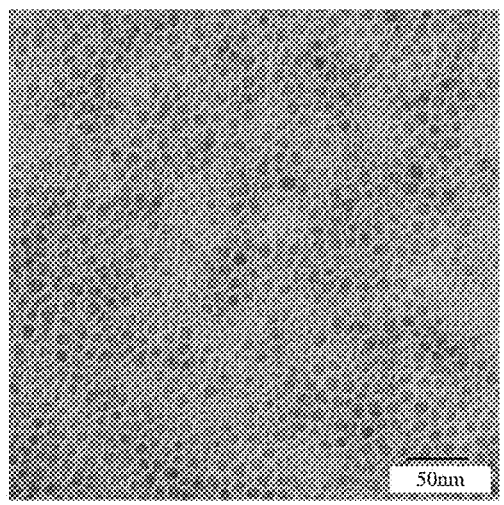
Figure 4C:
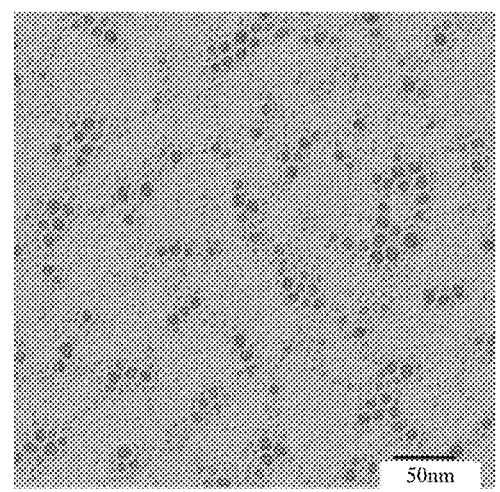

As shown in FIGS. 4A to 4C, the nanoparticles capsulating EGFR siRNAs in 2 milligrams per milliliter and photosensitizers in 32 milligrams per milliliter cannot form spherical particles stably (as shown in FIG. 4A). Conversely, the nanoparticles capsulating EGFR siRNAs in 2 milligrams per milliliter and photosensitizers in 16 milligrams per milliliter (as shown in FIG. 4B), and the nanoparticles capsulating EGFR siRNAs in 1 milligram per milliliter and photosensitizers in 16 milligrams per milliliter (as shown in FIG. 4C) can form spherical particles stably.

The result shows the maximum capsulating amount of the nanoparticle is siRNAs in 2 milligrams per milliliter and photosensitizers in 16 milligrams per milliliter. Following experimental examples are analyzed based on the nanoparticles having the maximum capsulating amount.

Third Experimental Example: Particle Sizes of Nanoparticles

After the nanoparticles having the maximum capsulating amount are prepared, the transmission electron microscope is provided for analyzing the size of the nanoparticles.

Figure 5A:
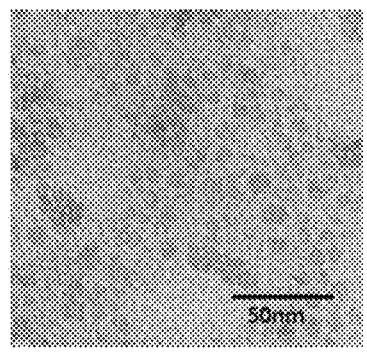
FIGS. 5A to 5F are electronic micrographs described in a third experimental example, wherein particles shown in FIGS. 5A, 5C, and 5E are the cores of the nanoparticles (including the inner lipid layer), particles shown in FIGS. 5B, 5D, and 5F are the nanoparticles including the inner lipid layer and the outer lipid layer; the particles shown in FIGS. 5A and 5B include EGFR siRNA, the particles shown in FIGS. 5C and 5D include the pyro-PA molecule, and the particles shown in FIGS. 5E and 5F include both EGFR siRNA and the pyro-PA molecule, all the photos are analyzed and displayed by the transmission electron microscopy.
Figure 5B:
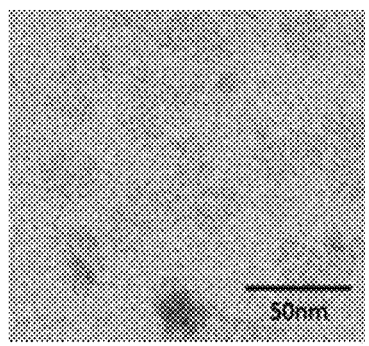
Figure 5C:
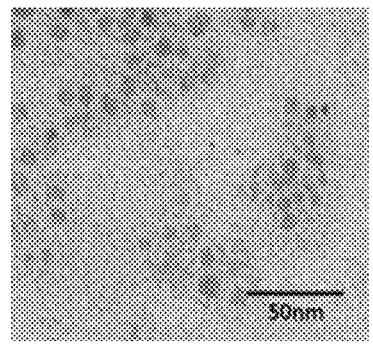
Figure 5D:
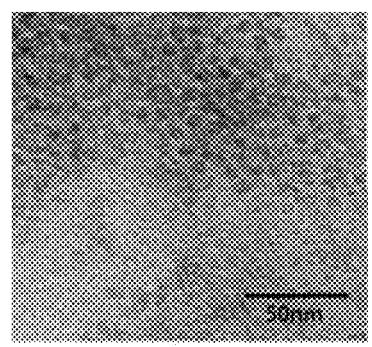
Figure 5E:
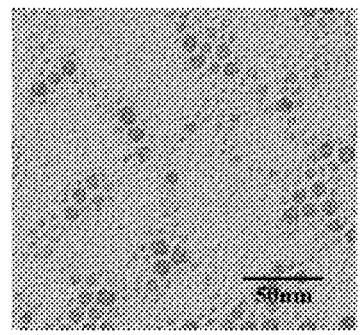
Figure 5F:
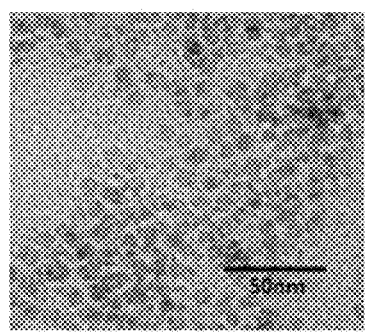

As shown in FIGS. 5A to 5F, the average diameter of the core capsulating EGFR siRNAs (including the inner lipid layer) is 11.1±3.1 nm (as shown in FIG. 5A), the average diameter of the nanoparticle capsulating EGFR siRNAs is 34.9±3.0 nm (as shown in FIG. 5B), the average diameter of the core capsulating the pyro-PA molecules (including the inner lipid layer) is 9 to 12 nm (as shown in FIG. 5C), and the average diameter of the nanoparticle capsulating the pyro-PA molecules is 15 to 20 nm (as shown in FIG. 5D). The average diameter of the core capsulating EGFR siNRAs and the pyro-PA molecules (including the inner lipid layer) is 9 to 12 nm (as shown in FIG. 5E), and the average diameter of the nanoparticle capsulating EGFR siNRAs and the pyro-PA molecules is 20 nm (as shown in FIG. 5F).

Fourth Experimental Example: Surface Potentials of Nanoparticles

After the nanoparticles having the maximum capsulating amount are prepared, the particle size analyzer (model: Zetasizer Nano S90, Malvern, Zurich, Switzerland) is also provided for measuring the surface potentials of the nanoparticles for analyzing the physical properties of the nanoparticles.

As shown in Table 1, the average surface potential of the nanoparticle without the AA molecules is 25.0±0.5 mV; conversely, the average surface potential of the nanoparticle with the AA molecules is 45.4±4.5 mV

TABLE 1

| surface potentials of the nanoparticles | | |
|---|---|---|
| test | With anisamide Surface potential (mV) | Without anisamide Surface potential (mV) |
| 1 | 49.2 | 25.7 |
| 2 | 46.7 | 24.6 |
| 3 | 40.4 | 24.8 |
| Average[a] | 45.4 ± 4.5 | 25.0 ± 0.5 |

[a]average value ± standard deviation (number is 3)

The result shows the surface potentials of the nanoparticles increase as the AA molecules are added into the nanoparticles. In other words, the addition of the AA molecules improves the stability of the nanoparticles and the dispersion of the nanoparticles.

Figure 6:
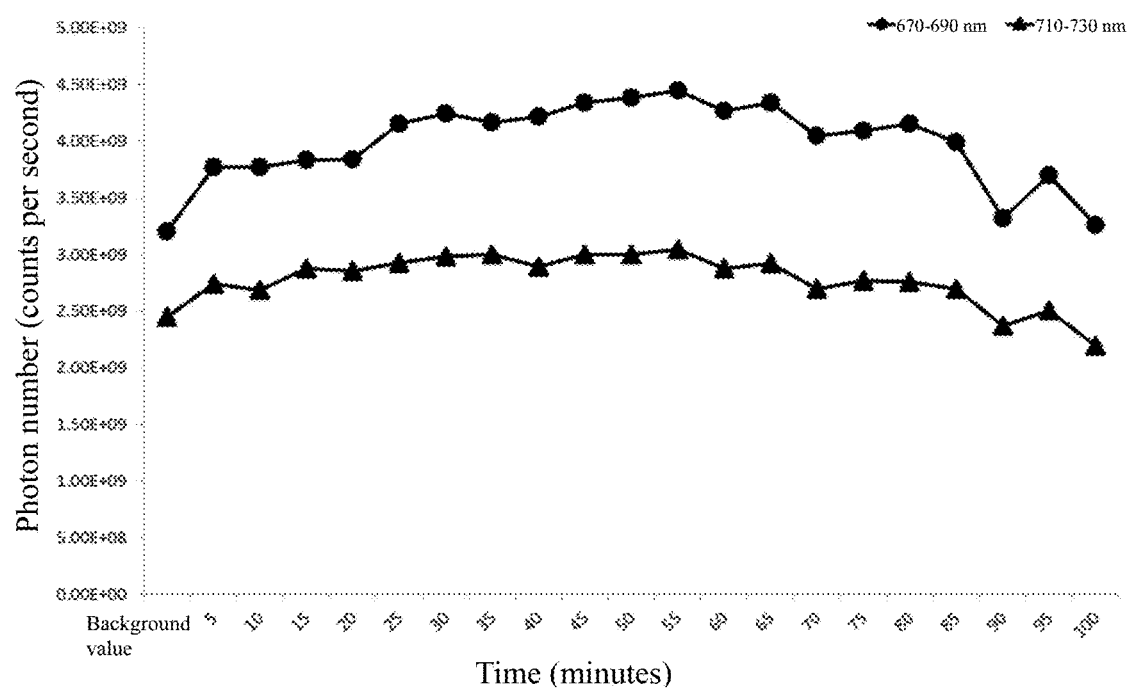
FIG. 6 illustrates a graph indicating the count per second (cps) of the nanoparticle of a fifth experimental example in certain wavelengths, wherein the nanoparticles are injected into mice and excited by a light having a wavelength of 410 nm, and the count per second of the nanoparticles in 670-690 nm and in 710-730 nm are monitored.

Fifth Experimental Example: Targeting the Nanoparticles to the Tumor and the Time Required for Doing so As mentioned, the nanoparticles is excited by a light having a wavelength of 410 nm, and the emission light of the nanoparticles can be detected from 670 to 690 nm and from 710 to 730 nm. FIG. 6 illustrates a graph indicating the photon number (in the unit of count per second (cps)) of emission of the nanoparticles of the fifth experimental example in 670-690 nm and in 710-730 nm, so that the time required for the nanoparticle arrival or accumulation to the tumor can be analyzed. The result shows, no matter which wavelengths of light is provided for measuring the photon number of the emission around the tumor, the nanoparticles start accumulating by 5 minutes after being injected into the subject and the accumulation of the nanoparticles become maximum after 55 minutes.

The result shows that the nanoparticles can be targeted to the tumor accurately, and the amount of the nanoparticles targeted to the tumor becomes maximized after 55 minutes of the injection.

Sixth Experimental Example: Treating the Tumor by Nanoparticles

As acknowledged from the fifth experimental example, after the intravenous injection, the nanoparticles will be accumulated at the tumor, and the amount of the accumulated nanoparticles becomes maximized after 55 minutes of the injection. As a result, in the sixth experimental example, a 55-minute time interval is provided for the interval between dosages of the photodynamic therapy.

Figure 7:
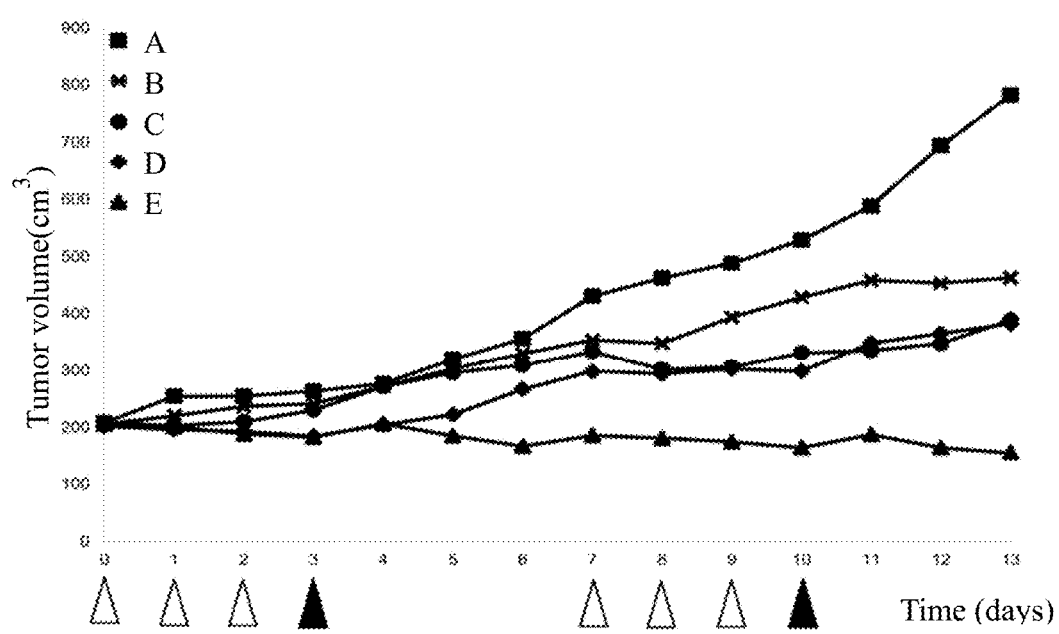
FIG. 7 illustrates daily volume changes of the tumors of nude mice having xenograft SCC4 oral cancer cells from day 1 to day 13.

FIG. 7 illustrates daily volume changes of the tumors of nude mice having xenograft SCC4 oral cancer cells from day 1 to day 13. The hollowed triangle marks (A) denote that the LCP-EGFR siRNA, the LCP-control siRNA, or the phosphate buffer saline (PBS) is injected into the tail veins of the nude mice, while the solid triangle marks denote that the LCP-pyro-PA is injected into the tail veins of the nude mice, with or without light illumination. For the in vivo animal experiments, nude mice having xenograft SCC4 oral cancer cells are provided for proving the therapeutic efficacy. Nude mice (BALB/c) having transplanted SCC4 oral cancer cells are used, and the experiments are preformed after the tumors grow to 200 cubic millimeters. The nude mice are divided into five groups, group A: control group (PBS); group B: photodynamic control group (LCP-control siRNA+photodynamic reagent (PDT)); group C: EGFR siRNA control group (LCP-EGFR siRNA+LCP-pyro-PA no light); group D: EGFR siRNA control group (LCP-EGFR siRNA+PBS light); and group E: therapeutic group (LCP-EGFR siRNA+PDT). Successive 14 days (i.e., from day 0 to day 13) are taken for observing the growth of the tumor.

At the fourteenth day (i.e., day 13), the tumor volume of the group A is 782.6 mm$^3$. The tumor volume of the group B is 462.2 mm$^3$, less than that of the group A by 320.4 mm$^3$. Therefore, the tumor suppression ratio by PDT is 40.9%. The tumor volume of the group C is 388.7 mm$^3$, less than that of the group A by 393.9 mm$^3$. The tumor suppression ratio of the group C is 50.3%. The tumor volume of the group D is 381.8 mm$^3$, less than that of the group A by 400.8 mm$^3$. The tumor suppression ratio of the group D is 51.2% ($p<0.001$). The tumor volume of the group E is 155.6 mm$^3$, less than that of the group A by 627.0 mm$^3$. The tumor suppression ratio of the group E is 80.1%. Therefore, as compared with other groups (including groups applying one of the EGFR siRNA and PDT individually), group E has the best suppression performance for the growth of the cancer tumors.

Accordingly, as reveled by the result, the nanoparticles having EGFR siRNA have the ability for suppressing the tumor growth. Additionally, once a light with proper wavelengths is provided for illuminating the nanoparticles to perform photodynamic therapy and achieves a better therapeutic efficacy.

Based on the above, in some embodiments, the nucleic acids, the medical nanoparticles having the nucleic acid, and/or the pharmaceutical compositions thereof can be applied to suppress the expressions and the functions of the EGFR by the nucleic acid (for example, a small hairpin ribonucleic acid), so that the growth of the cancer cells can be suppressed and/or the death of the cancer cells can be promoted. In some embodiments, the photosensitizer in the medical nanoparticle will release free radicals after being illuminated or excited by a light having certain wavelengths and the free radicals will cause the oxidative damages of cell targets to achieve the therapeutic efficacy on tumors. In some embodiments, the photosensitizer in the medical nanoparticle is suitable for the cancer diagnosis. In addition, in some embodiments, because of the coexistence of the nucleic acid and the photosensitizer, the nucleic acid and the photosensitizer can be applied to cure the tumor by different suppressing paths to achieve a better therapeutic efficacy.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A medical nanoparticle, comprising:
   a core, comprising a bio-degradable ionic precipitate (BIP);
   an outer lipid layer;
   an inner lipid layer between the core and the outer lipid layer; and
   a nucleic acid at the surface of the core, wherein the nucleic acid comprises a nucleotide sequence having the sequence set forth in SEQ ID NO: 1.

2. The medical nanoparticle according to claim 1, further comprising a lipid-polyethylene glycol (PEG) conjugate linked to the outer lipid layer.

3. The medical nanoparticle according to claim 2, wherein the lipid-PEG conjugate comprises a lipid selected from a group consisting of 1,2-dimyristoyl-sn-glycero-3-phosphoethanolamine (DMPE), 1,2-distearoyl-sn-glycero-3-phosphoethanolamine (DSPE), 1,2-dilauroyl-sn-glycero-3-phosphoethanolamine (DLPE), cholesterol, oleic acid, and derivatives thereof.

4. The medical nanoparticle according to claim 2, further comprising a target agent linked to the lipid-PEG conjugate.

5. The medical nanoparticle according to claim 4, wherein the target agent is a benzamide derivative.

6. A medical nanoparticle, comprising:
   a core, comprising a bio-degradable ionic precipitate (BIP);
   an outer lipid layer;
   an inner lipid layer between the core and the outer lipid layer; and
   a nucleic acid being capable of suppressing expressions and functions of an epidermal growth factor receptor, wherein the nucleic acid is at the surface of the core,
   wherein the nucleic acid comprises a nucleotide sequence having the sequence set forth in SEQ ID NO: 1, and
   wherein the medical nanoparticle further comprises a photosensitizer, the photosensitizer is selected from a group consisting of pyropheophorbide-phosphatidic acid (pyro-PA), photosan, photofrin (PH), tin etiopurpurin (SnET2), benzoporphyrin derivative (BPD), and 5-aminolaevulinic acid (ALA).

7. The medical nanoparticle according to claim 6, further comprising a lipid-polyethylene glycol (PEG) conjugate linked to the outer lipid layer.

8. The medical nanoparticle according to claim 7, wherein the lipid-PEG conjugate comprises a lipid selected from a group consisting of 1,2-dimyristoyl-sn-glycero-3-phosphoethanolamine (DMPE), 1,2-distearoyl-sn-glycero-3-phosphoethanolamine (DSPE), 1,2-dilauroyl-sn-glycero-3-phosphoethanolamine (DLPE), cholesterol, oleic acid, and derivatives thereof.

9. The medical nanoparticle according to claim 7, further comprising a target agent linked to the lipid-PEG conjugate.

10. The medical nanoparticle according to claim 7, wherein the target agent is a benzamide derivative.

11. The medical nanoparticle according to claim 1, wherein the BIP is selected from a group consisting of calcium phosphate, calcium citrate, calcium carbonate, magnesium carbonate, magnesium phosphate, and manganese phosphate.

12. The medical nanoparticle according to claim 6, wherein the BIP is selected from a group consisting of calcium phosphate, calcium citrate, calcium carbonate, magnesium carbonate, magnesium phosphate, and manganese phosphate.

13. The medical nanoparticle according to claim 1, wherein the inner lipid layer is an anion lipid layer and the outer lipid layer is a cation lipid layer.

14. The medical nanoparticle according to claim 6, wherein the inner lipid layer is an anion lipid layer and the outer lipid layer is a cation lipid layer.

15. The medical nanoparticle according to claim 1, wherein the inner lipid layer is an anion lipid layer and the outer lipid layer is a neutral lipid layer.

16. The medical nanoparticle according to claim 6, wherein the inner lipid layer is an anion lipid layer and the outer lipid layer is a neutral lipid layer.

17. A pharmaceutical composition, comprising:
    the medical nanoparticle according to claim 1; and
    a pharmaceutically acceptable excipient.

18. A pharmaceutical composition, comprising:
    the medical nanoparticle according to claim 6; and
    a pharmaceutically acceptable excipient.

* * * * *